(12) United States Patent
Giles et al.

(10) Patent No.: US 8,530,399 B2
(45) Date of Patent: *Sep. 10, 2013

(54) CONDITIONING SHAMPOO COMPOSITIONS

(75) Inventors: Colin Christopher David Giles, Changning District (CN); Anuchai Sinsawat, Changning District (CN)

(73) Assignee: Conopco Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/513,677

(22) PCT Filed: Oct. 30, 2007

(86) PCT No.: PCT/EP2007/061678
§ 371 (c)(1),
(2), (4) Date: May 6, 2009

(87) PCT Pub. No.: WO2008/055816
PCT Pub. Date: May 15, 2008

(65) Prior Publication Data
US 2010/0029528 A1   Feb. 4, 2010

(30) Foreign Application Priority Data
Nov. 8, 2006 (EP) .................... 06123679

(51) Int. Cl.
| | | |
|---|---|---|
| *C11D 1/02* | (2006.01) | |
| *C11D 1/62* | (2006.01) | |
| *C11D 3/02* | (2006.01) | |
| *C11D 3/20* | (2006.01) | |

(52) U.S. Cl.
USPC ........... 510/125; 510/127; 510/137; 510/138; 510/488; 510/501; 510/504; 510/505; 510/506; 424/70.19; 424/70.22; 424/70.24; 424/70.28

(58) Field of Classification Search
USPC ................. 510/125, 127, 137, 138, 488, 501, 510/504, 505, 506; 424/70.19, 70.22, 70.24, 424/70.28
See application file for complete search history.

(56) References Cited

U.S. PATENT DOCUMENTS

| | | | |
|---|---|---|---|
| 4,390,033 | A | 6/1983 | Khalil et al. |
| 5,034,218 | A | 7/1991 | Duvel |
| 6,617,292 | B2 | 9/2003 | Perron et al. |
| 2003/0223952 | A1 | 12/2003 | Wells et al. |

FOREIGN PATENT DOCUMENTS

| | | | |
|---|---|---|---|
| JP | 2004-307463 | * | 11/2004 |
| WO | 03/047541 | | 6/2003 |
| WO | 05/039517 A | | 5/2005 |

OTHER PUBLICATIONS

English Language Machine Translation of JP 2004-307463.*
English Language Human Translation of JP 2004-307463.*
European Search Report on Application No. EP 06 12 3679 dated May 14, 2007.
International Search Report on Application No. PCT/EP2007/061678 dated Feb. 27, 2008.
Database WPI, XP002432836 & JP 2004 307463 A, (2004) abstract
"Wikipedia: aluminum oxide", XP002433100, Retrieved from Internet May 2007, 4 pages.
Co-Pending application for: Applicants: Giles et al.; U.S. Appl. No. 12/513,676; filed May 6, 2009, entitled Conditioning Shampoo Compositions.

* cited by examiner

*Primary Examiner* — Gregory Delcotto
(74) *Attorney, Agent, or Firm* — Ronald A. Koatz

(57) ABSTRACT

An aqueous conditioning shampoo composition comprising an anionic cleansing surfactant and a gel network comprising: (i) a fatty material selected from $C_{12}$-$C_{22}$ fatty alcohol, $C_{12}$-$C_{22}$ fatty acid, $C_{12}$-$C_{22}$ fatty amide or mixtures thereof and (ii) hydrophobic particulates having a melting point of greater than that of the fatty material.

4 Claims, No Drawings

CONDITIONING SHAMPOO COMPOSITIONS

FIELD OF THE INVENTION

This invention relates to aqueous conditioning shampoo compositions comprising a cleansing surfactant and a gel network.

BACKGROUND AND PRIOR ART

Conditioning shampoo compositions comprising various combinations of cleansing surfactant and conditioning agents are known. These products typically comprise an anionic cleansing surfactant in combination with a conditioning agent. Amongst the most popular conditioning agents used in shampoo compositions are oily materials such as mineral oils, naturally occurring oils such as triglycerides and silicone polymers. These are generally present in the shampoo as dispersed hydrophobic emulsion droplets. Conditioning is achieved by the oily material being deposited onto the hair resulting in the formation of a film. Such compositions often have a relatively low viscosity and may be perceived to be low quality as a result.

Other conditioning shampoo compositions use gel networks comprising fatty alcohol to structure or thicken the product and also to deliver a conditioning benefit. US 2003/0223952 (P&G) discloses conditioning shampoos comprising detersive surfactant and a gel network made from fatty alcohol and a cationic surfactant.

The use of particulate materials in conditioning shampoos is not common. U.S. Pat. No. 6,617,292 B2 (L'Oreal) discloses conditioning shampoos comprising aluminium oxide, an amphoteric or nonionic surfactant, a fatty acid or fatty alcohol, and a cationic surfactant.

A problem that arises with many of the conditioners disclosed in the prior art is that they do not give good sensory benefits both when the hair is wet, i.e., during and/or immediately after application and also when the hair is subsequently dried.

SUMMARY OF THE INVENTION

The present inventors have found that excellent sensory benefits may be given to both wet and subsequently dried hair by use of conditioning shampoos comprising an anionic cleansing surfactants and a particularly structured gel network. These conditioning shampoos also have the benefit of having a rich, creamy appearance, enhancing their perception of being high quality products.

Conditioning shampoo compositions of the invention give good wet feel and ease of wet combing. In addition they give good dry feel, ease of dry combing, and manageability.

In a first aspect of the invention, there is provided an aqueous conditioning shampoo composition comprising an anionic cleansing surfactant and a gel network comprising:
 (i) a fatty material selected from $C_{12}$-$C_{22}$ fatty alcohol, $C_{12}$-$C_{22}$ fatty acid, $C_{12}$-$C_{22}$ fatty amide or mixtures thereof; and
 (ii) hydrophobic particulates having a melting point of greater than that of the fatty material.

In a second aspect of the invention, there is provided a method of cleansing and conditioning the hair comprising the application of an aqueous conditioning shampoo composition according to the first aspect of the invention.

In a third aspect of the invention, there is provided the use of a gel network comprising a fatty material selected from $C_{12}$-$C_{22}$ fatty alcohol, $C_{12}$-$C_{22}$ fatty acid, $C_{12}$-$C_{22}$ fatty amide or mixtures thereof and hydrophobic particulates having a melting point of greater than that of the fatty material to give structure and/or conditioning benefits to an aqueous shampoo composition comprising an anionic cleansing surfactant.

In a fourth aspect of the invention, there is provided a method of manufacturing an aqueous conditioning shampoo composition comprising the preparation of a gel network comprising a fatty material selected from $C_{12}$-$C_{22}$ fatty alcohol, $C_{12}$-$C_{22}$ fatty acid, $C_{12}$-$C_{22}$ fatty amide or mixtures thereof and hydrophobic particulates having a melting point of greater than that of the fatty material, the gel network being subsequently added to an aqueous solution of an anionic cleansing surfactant.

DETAILED DESCRIPTION OF THE INVENTION

The compositions of the invention are suitable for application to the human hair. They are typically used as rinse off products, that is to say their application is usually followed by a rinsing stage with water.

The invention uses a gel network as described hereinafter to deliver structure and conditioning benefits to a shampoo composition comprising an anionic cleansing surfactant. The term "structure", when used in this context, should be understood to mean "thicken", i.e. increase the viscosity thereof.

The preferred viscosity for products according to the invention is from 3000 to 9000 cP (mPa·s), more preferably from 5000 to 7000 cP (mPa·s), and most preferably from 5500 to 6500 cP (mPa·s) at 30° C., as measured by a Brookfield viscometer equipped with a RVT pin number 5 at a measuring speed of 20 rpm.

By "aqueous conditioning shampoo composition" is meant a composition which has water or an aqueous solution or a lyotropic liquid crystalline phase as its major component. Typically, the composition will comprise at least 50%, preferably at least 60%, at most preferably at least 75% by weight of water.

Anionic Cleansing Surfactant

Conditioning shampoo compositions according to the invention comprise one or more anionic cleansing surfactants, which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic cleansing surfactants are sodium lauryl sulphate, sodium lauryl ether sulphate(n)EO, (where n is from 1 to 3), sodium lauryl ether sulphosuccinate(n)EO, (where n is from 1 to 3), ammonium lauryl sulphate, ammonium lauryl ether sulphate(n)EO, (where n is from 1 to 3), sodium cocoyl isethionate and lauryl ether carboxylic acid(n) EO (where n is from 10 to 20).

Mixtures of any of the foregoing anionic cleansing surfactants may also be suitable.

The total amount of anionic cleansing surfactant preferably ranges from 0.5 to 45%, more preferably from 1 to 30%, and most preferably from 5 to 20% by total weight of the composition.

Gel Network

The gel network is formed by combining the components at a temperature above the melting point of the fatty material in the presence of water. In a preferred method of manufacture in accordance with the fourth aspect of the invention, the fatty material is melted in water and the particulate material is then added. In a more preferred method of manufacture, a quaternary ammonium compound is also added, preferably after the particulate material. A dispersion of liquid crystalline phase droplets is typically produced. It will be realised that, in effect, the gel network has another component: water. In preferred embodiments, the gel network comprises an $L_\beta$ lamellar phase dispersion at 25° C.

The composition according to the invention can only be formed with a separately made gel network. Mixing the components of the gel network together without premixing and heating does not form a gel network.

Fatty Material

A fatty material selected from $C_{12}$-$C_{22}$, preferably $C_{16\text{-}22}$ fatty alcohol, $C_{12}$-$C_{22}$, preferably $C_{16\text{-}22}$ fatty acid, $C_{12}$-$C_{22}$, preferably $C_{16\text{-}22}$ fatty amide or mixtures thereof is an essential component of the gel network. Preferably, the fatty material comprises a $C_{12}$-$C_{22}$ fatty alcohol. The fatty alcohol is preferably a primary alcohol. The fatty alcohol and/or fatty acid and/or amide preferably has a linear (i.e. non-branched) hydrocarbon chain. Preferably, said chain is saturated. Preferably, the fatty alcohol and/or fatty acid and/or fatty amide is $C_{16}$-$C_{22}$ and more preferably it is $C_{16}$-$C_{18}$. Most preferably the fatty material is cetyl alcohol and/or stearyl alcohol.

The total amount of fatty material selected from $C_{12}$-$C_{22}$ fatty alcohol, $C_{12}$-$C_{22}$ fatty acid, or mixtures thereof, is preferably from 0.01 to 20%, more preferably from 0.1 to 10%, and most preferably from 0.5 to 5% by weight of the total composition. In preferred embodiments, these preferred amounts apply to the level of $C_{12}$-$C_{22}$ fatty alcohol in the total composition.

Hydrophobic Particulates

Hydrophobic particulates having a melting point of greater than that of the fatty material are a second essential component of the gel network. Preferably, the particulates have a melting point of greater than 150° C. Without wishing to be bound by theory, it is believed that such particulates act as templates that help sustain the ordered structure of the gel network within the shampoo composition, despite the presence of anionic surfactant therein. The particles are believed to enhance the stability and performance of the gel network as a result.

The particulates are solids with a melting point of greater than that of the fatty material referred to above. This is important for giving stability to the gel network and for enabling its formation, the gel network typically being prepared at elevated temperature. When the gel network also comprises a quaternary ammonium compound (vide infra), the particulates also have a melting point higher than this component.

The term "hydrophobic" should be understood to mean that the particulates lack an affinity for water; in particular, that they have a solubility in water of less than 0.01 g/l and that they are not dispersible in water without continual agitation. Typically, the hydrophobic particulates partition into n-octanol rather than water, when shaken at 25° C. in a 1:1 mixture by volume of these liquids; that is to say, the majority (greater than 50%) and more typically greater than 90% of the particulates partition in this manner.

It is believed that the hydrophobicity of the particulates enhances their interaction with fatty components of the gel network and leads to a more stable gel network and a more stable and effective composition.

Suitable hydrophobic particulates may be inorganic, organic, or of mixed inorganic/organic nature.

Suitable hydrophobic particulates include clays, hydrophobically modified acrylates, zinc pyrithione, hydrophobically modified cellulose, hydrophobically modified silica, hexafluoropropylene/tetrafluoroethylene copolymer, PTFE, styrene/acrylates, nylon, polyurethane, polyvinylchloride, polymethylmethacrylate, aluminium starch octenylsuccinate, acrylates, ammonium acrylates, cellulose, dextran, silica, carbomer, chalk, chitosan, titanium dioxide, titanium hydroxide, alumina and mixtures thereof.

Preferred hydrophobic particulates are hydrophobically-modified natural clays and synthetic clays. The term clay refers to materials comprising particles having a net electrostatic charge on at least one surface. The clays may be anionic or cationic, i.e., they may have a net charge on the surface of the clay that is negative or positive, respectively.

Preferred hydrophobically-modified clays are based upon anionic clays, such as smectite clays.

Smectite clays are, for example, disclosed in U.S. Pat. Nos. 3,862,058, 3,948,790, 3,954,632 and 4,062,647 and in EP-A-299,575 and EP-A-313,146, all in the name of Procter & Gamble Company.

Typical smectite clays include the compounds having the general formula $Al_2(Si_2O_5)_2(OH)_2.nH_2O$ and the compounds having the general formula $Mg_3(Si_2O_5)_2(OH)_2.nH_2O$, and derivatives thereof, for example in which a proportion of the aluminium ions are replaced with magnesium ions or a proportion of the magnesium ions are replaced with lithium ions and/or some of the hydroxyl ions are replaced by fluoride ions; the derivatives may comprise a further metal ion to balance the overall charge.

Specific examples of suitable smectite clays are montmorillonites, volchonskoites, nontronites, saponites, beidelites and sauconites, particularly those having an alkali or alkaline earth metal ion within the crystal lattice structure. Preferred smectite clays are montmorillonites, nontronites, saponites, beidelites, sauconites and mixtures thereof. Particularly preferred are montmorillonites, e.g. bentonites and hectorites, with bentonites being especially preferred.

Hydrophobically-modified clays are derivable from clays by modification of the clay with a hydrophobic material. Typically, the modification entails replacing at least a proportion of the inorganic metal ions of the unmodified clay with organic cations. Preferred organic cations for this purpose comprising one or more $C_6$-$C_{30}$ alkyl groups. The cationic group is preferably a quaternary ammonium group. Particularly preferred organic cations have two $C_6$-$C_{30}$ alkyl groups, for example: distearyldimethylammonium; dicetyldimethylammonium; dimethyldi(hydrogenated tallow)ammonium; dicetylmethylbenzylammonium; dicocodimethylammonium; dibehenyl/diarachidyldimethylammonium; hydroxypropyl bis-stearylammonium; dibehenyldimethylammonium; dibehenylmethylbenzylammonium; and dimyristyldimethylammonium.

Especially preferred hydrophobically-modified clays are Quaternium-18 Bentonite, i.e. bentonite hydrophobically-modified by dimethyldi(hydrogenated tallow)ammonium cations) and Quaternium-90 Bentonite, an analogous material with two vegetable-derived fatty chains. Examples of such clays are Tixogel MP 100™ and Tixogel MP 100V from Sud Chemie. Other similar materials include Quaternium benzalkonium bentonite, Quaternium-18 hectorite, stearalkonium bentonite, stearalkonium hectorite and dihydrogenated tallow benzylmonium hectorite.

The hydrophobic particulates having a melting point of greater than that of the fatty material have a particle size such that preferably at least 50% and more preferably at least 80% of them are able to pass through a 90 micron screen, such as an air sieve as commonly used in the art.

The total amount of hydrophobic particulates having a melting point of greater than that of the fatty material is preferably from 0.005 to 10%, more preferably from 0.01 to 5%, and most preferably from 0.01 to 1% by weight of the total composition.

The weight ratio of particles having platelet morphology to the fatty material is preferably from 1:100 to 1:2, more preferably from 1:50 to 1:5, and most preferably from 1:30 to 1:10.

Quaternary Ammonium Compound

A quaternary ammonium compound having at least one carbon chain of length $C_{12}$-$C_{30}$ is a highly preferred component of the gel network. In preferred embodiments, the quaternary ammonium compound has only one carbon chain of length $C_{12}$-$C_{30}$. Typically, the one carbon chain of length $C_{12}$-$C_{30}$ is a linear (i.e. non-branched) hydrocarbon chain. Preferably, the one carbon chain of length $C_{12}$-$C_{30}$ is saturated. Preferably, the one carbon chain of length $C_{12}$-$C_{30}$ is of chain length $C_{12}$-$C_{22}$ and more preferably it is of chain length $C_{16}$-$C_{22}$.

The quaternary ammonium compound having at least one carbon chain of length $C_{12}$-$C_{30}$ has three other carbon-containing substituents attached to the quaternary nitrogen atom. These are typically $C_1$-$C_4$ alkyl groups and are preferably methyl and/or ethyl groups; most preferably they are methyl groups.

Most preferably, the quaternary ammonium compound having at least one carbon chain of length $C_{12}$-$C_{30}$ is cetyltrimethylammonium chloride or benhenyltrimethylammonium chloride.

When present, the total amount of quaternary ammonium compound having at least one carbon chain of length $C_{12}$-$C_{30}$ is preferably from 0.005 to 10%, more preferably from 0.01 to 5%, and most preferably from 0.01 to 1% by weight of the total composition.

The weight ratio of quaternary ammonium compound having at least one carbon chain of length $C_{12}$-$C_{30}$ to the hydrophobic particulates is preferably from 30:1 to 5:1.

The molar ratio of quaternary ammonium compound having at least one carbon chain of length $C_{12}$-$C_{30}$ to fatty material selected from $C_{12}$-$C_{22}$ fatty alcohol, $C_{12}$-$C_{22}$ fatty acid, or mixtures thereof is preferably from 1:100 to 5:1, more preferably from 1:50 to 1:2, and most preferably from 1:30 to 1:10. These molar ratios apply particularly when the quaternary ammonium compound has only one carbon chain of length $C_{12}$-$C_{30}$ and the fatty material is a $C_{12}$-$C_{22}$ fatty alcohol.

Silicone Oils

A preferred optional component in conditioning shampoo compositions according to the invention is silicone oil. Silicone oil can enhance the conditioning benefit found with compositions of the invention.

When used, silicone oil is typically present as emulsified droplets having a mean droplet diameter ($D_{3,2}$) of 4 micrometers or less. Preferably the mean droplet diameter ($D_{3,2}$) is 1 micrometer or less, more preferably 0.5 micrometer or less, and most preferably 0.25 micrometer or less.

A suitable method for measuring the mean droplet diameter ($D_{3,2}$) is by laser light scattering using an instrument such as a Malvern Mastersizer.

Preferably the silicone oil is non-volatile, meaning that it has a vapour pressure of less than 1000 Pa at 25° C.

Suitable silicone oils are polydiorganosiloxanes, in particular polydimethylsiloxanes (dimethicones), polydimethyl siloxanes having hydroxyl end groups (dimethiconols), and amino-functional polydimethylsiloxanes (amodimethicones).

Suitable silicones preferably have a molecular weight of greater than 100,000 and more preferably a molecular weight of greater than 250,000.

Suitable silicones preferably have a kinematic viscosity of greater than 50,000 cS ($mm^2 \cdot s^{-1}$) and more preferably a kinematic viscosity of greater than 500,000 cS ($mm^2 \cdot s^{-1}$). Silicone oil kinematic viscosities as referred to in this specification are measured at 25° C. and can be measured by means of a glass capillary viscometer as set out further in Dow Corning Corporate Test Method CTM004 Jul. 20, 1970.

Suitable silicones for use in compositions of the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788, DC-1310, DC-7123 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874.

Mixtures of any of the above described silicone emulsions may also be used.

The total amount of silicone oil in compositions of the invention may suitably range from 0.05 to 10%, particularly from 0.2 to 8%, and especially from 0.5 to 5% by weight of the composition.

Hydrocarbon Oils and Ester Oils

A further component that may be used in compositions of the invention is a hydrocarbon oil or ester oil. Like silicone oils, these materials may enhance the conditioning benefits found with compositions of the invention.

Suitable hydrocarbon oils have at least 12 carbon atoms, and include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Also suitable are polymeric hydrocarbons of $C_{2-6}$ alkenyl monomers, such as polyisobutylene.

Suitable ester oils have at least 10 carbon atoms, and include esters with hydrocarbyl chains derived from fatty acids or alcohols. Typical ester oils are formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Preferred fatty esters are mono-, di- and triglycerides, more specifically the mono-, di-, and tri-esters of glycerol with long chain carboxylic acids such as $C_{1-22}$ carboxylic acids. Examples of such materials include cocoa butter, palm stearin, sunflower oil, soyabean oil and coconut oil.

Mixtures of any of the above described hydrocarbon/ester oils also be used.

The total combined amount of hydrocarbon oil and ester oil in compositions of the invention may suitably range from 0.05 to 10%, particularly from 0.2 to 5%, and especially from 0.5 to 3% by weight of the composition.

Cationic Polymer

A preferred additional component in conditioning shampoo compositions according to the invention is a cationic polymer. Such components may enhance the deliver of conditioning agents and thereby improve the conditioning benefits obtained.

Cationic polymers typically contain cationic nitrogen-containing groups such as quaternary ammonium or protonated amino groups. The cationic protonated amines can be primary, secondary, or tertiary amines (preferably secondary or tertiary). The average molecular weight of the cationic polymer is preferably from 5,000 to 10 million. The cationic polymer preferably has a cationic charge density of from 0.2 meq/gm to 7 meq/gm.

The cationic nitrogen-containing moiety of the cationic polymer is generally present as a substituent on all, or more typically on some, of the repeat units thereof. The cationic polymer may be a homo-polymer or co-polymer of quaternary ammonium or cationic amine-substituted repeat units, optionally in combination with non-cationic repeat units. Non-limiting examples of such polymers are described in the CTFA Cosmetic Ingredient Dictionary, 6th edition, edited by Wenninger, J A and McEwen Jr, G N, (The Cosmetic, Toiletry, and Fragrance Association, 1995). Particularly suitable cationic polymers for use in the composition include polysaccharide polymers, such as cationic cellulose derivatives, cationic starch derivatives, and cationic guars.

Examples of cationic cellulose derivatives are salts of hydroxyethyl cellulose reacted with trimethylammonium substituted epoxide, referred to in the industry (CTFA) as Polyquaternium 10. Further examples of cationic cellulose derivatives are prepared from hydroxyethyl cellulose and lauryldimethylammonium-substituted epoxide and are referred to in the industry (CTFA) as Polyquaternium 24.

Especially preferred cationic polymers are cationic guar gum derivatives, such as guar hydroxypropyltrimonium chloride, specific examples of which include the JAGUAR series commercially available from Rhodia Corp. (e.g., JAGUAR C17 or JAGUAR C13S).

Other suitable cationic polymers include quaternary nitrogen-containing cellulose ethers, examples of which are described in U.S. Pat. No. 3,962,418. Other suitable cationic polymers include derivatives of etherified cellulose, guar and starch, some examples of which are described in U.S. Pat. No. 3,958,581.

Synthetic cationic polymers may also be employed. Examples include co-polymers of vinyl monomers having cationic protonated amine or quaternary ammonium functionality with water soluble spacer repeat units, typically derived from monomers such as acrylamide, methacrylamide, N-alkyl and N,N-dialkyl acrylamides and methacrylamides, alkyl acrylate, allyl methacrylate, vinyl caprolactone, vinyl acetate/alcohol. Other spacer repeat units may be derived from maleic anhydride, propylene glycol, or ethylene glycol.

Other suitable synthetic cationic polymers include co-polymers of 1-vinyl-2-pyrrolidone and 1-vinyl-3-methylimidazolium salt (e.g., chloride salt), referred to in the industry (CTFA) as Polyquaternium-16; co-polymers of 1-vinyl-2-pyrrolidone and dimethylaminoethyl methacrylate, refereed to in the industry (CTFA) as Polyquaternium-11; cationic diallyl quaternary ammonium-containing polymers, including, for example, dimethyldiallylammonium chloride homo-polymer and co-polymers of acrylamide and dimethyldiallylammonium chloride, referred to in the industry (CTFA) as Polyquaternium 6 and Polyquaternium 7, respectively; and mineral acid salts of amino-alkyl esters of homo-polymers and co-polymers of unsaturated carboxylic acids having from 3 to 5 carbon atoms.

The total amount of cationic polymer in the composition is preferably from 0.05% to 2% and more preferably from 0.1 to 0.5% by weight of the composition.

Amphoteric Surfactant

An amphoteric surfactant is a preferred additional ingredient in compositions of the invention. Suitable amphoteric surfactants are betaines, such as those having the general formula $R(CH_3)_2N^+CH_2CO_2^-$, where R is an alkyl or alkylamidoalkyl group, the alkyl group preferably having 10-16 carbon atoms. Particularly suitable betaines are oleyl betaine, caprylamidopropyl betaine, lauramidopropyl betaine, isostearylamidopropyl betaine, and cocoamidopropyl betaine.

Other suitable betaine amphoteric surfactants are sulfobetaines, such as those having the general formula $R'(CH_3)_2N^+CH_2CH(OH)CH_2SO_3^-$, where R' is an alkyl or alkylamidoalkyl group, the alkyl group preferably having 10-16 carbon atoms. Particularly suitable sulfobetaines are laurylamidopropyl hydroxysultaine and cocoamidopropyl hydroxysultaine.

Other suitable amphoteric surfactants are fatty amine oxides, such as lauryldimethylamine oxide.

When included, the total level of amphoteric surfactant is preferably from 0.1% to 20%, more preferably from 1% to 10%, and most preferably from 1% to 5% by weight of the composition.

Carbomer

A Carbomer may be advantageously employed in particular embodiments of the invention. A Carbomer is a homopolymer of acrylic acid crosslinked with an allyl ether of pentaerythritol or an allyl ether of sucrose. Such materials may serve as suspending agents.

When included, the total level of Carbomer is preferably from 0.01% to 10%, more preferably from 0.1% to 5%, and most preferably from 0.25% to 1% by weight of the composition.

Other Optional Components

Compositions according to the invention may contain other ingredients suitable for use in hair cleansing and conditioning compositions. Such ingredients include but are not limited to: fragrance, suspending agents, amino acids and protein derivatives, viscosity modifiers (e.g. electrolytes, such as sodium chloride), preservatives (e.g. formaldehyde), colourants, and pearlescers (e.g. ethylene glycol distearate or mica).

EXAMPLES

Example 1 as indicated in Table 1 was prepared in the following manner.

At least 10% of the water was heated to 65° C. in a side pot. To this, was added the cetyl alcohol, with high speed stirring. When all of the cetyl alcohol had melted, the Quaternium-18 Bentonite was added, also with high speed stirring, followed by the cetyltrimethylammonium chloride. The uniform dispersion obtained, whilst still at 65° C., was added to an aqueous solution of the sodium laureth sulphate at ambient temperature. Moderate speed stirring was employed to achieve a uniform dispersion without causing aeration of the product. The remaining components were then added with continued moderate speed stirring.

Comparative Example A was prepared by methods known in the art.

TABLE 1

| Component | Comparative Example A | Example 1 |
| --- | --- | --- |
| Sodium laureth sulphate (1) | 12.00 | 12.00 |
| Cocoamidopropyl betaine | 1.60 | 1.60 |
| Guar hydroxypropyl trimonium chloride | 0.20 | 0.20 |
| Cetyl alcohol | — | 2.00 |
| Cetyl trimethylammonium chloride | — | 0.10 |
| Quaternium-18 bentonite (2) | — | 0.10 |
| Carbomer | 0.40 | 0.40 |
| Ethylene glycol distearate | 0.60 | 0.60 |
| Dimethiconol | 2.00 | 2.00 |
| Fragrance | 0.70 | 0.70 |
| Formaldehyde | 0.04 | 0.04 |
| Sodium chloride | 0.75 | 0.75 |
| Chlorinated water | To 100 | To 100 |

(1) Sodium lauryl ether sulphate (1EO).
(2) Tixogel MP100V ™, ex Sud Chemie.

All ingredients are expressed by weight percent of the total composition, and as level of active ingredient.

Comparative Example A and Example 1 were compared in a salon halfhead test assessed by hairdressers (n=36). Example 1 was found to be significantly superior on a wide range of conditioning benefits, including ease of fingering through (wet); slippery feel (wet); soft feel (wet); ease of wet combing; slippery feel (dry); soft feel (dry); more elastic compressed; weighty hair; and retain style.

In a subsequent test, Example 1 was compared with an analogous composition in which the Quaternium-18 bentonite was not included. In this test, Example 1 was again found to be significantly superior on a wide range of conditioning benefits, including soft feel (wet); slippery feel (dry); straight weighty (dry); bouncy (dry); retain manageability (next day).

The invention claimed is:

1. An aqueous conditioning shampoo composition comprising 5 to 30% by wt. anionic cleansing surfactant and a gel network comprising:
   (i) a fatty material selected from $C_{12}$-$C_{22}$ fatty alcohol, $C_{12}$-$C_{22}$ fatty acid, $C_{12}$-$C_{22}$ fatty amide or mixtures thereof and
   (ii) hydrophobic particulates having a melting point of greater than that of the fatty material wherein said particulate is a hydrophobically modified clay selected from the group consisting of hydrophobically modified bentonite, hydrophobically modified hectorite and mixtures thereof; and
   (iii) water
   wherein said aqueous shampoo comprises 60% or greater water
   wherein the gel network is a separately made network in which components of the network are premixed and heated to form said network.

2. An aqueous conditioning shampoo composition according to claim 1, wherein the gel network comprises a quaternary ammonium compound having at least one carbon chain of length $C_{12}$-$C_{30}$ and wherein the hydrophobic particulates have a melting point higher than said quaternary ammonium compound.

3. An aqueous conditioning shampoo composition according to claim 1, wherein the gel network comprises a $C_{12}$-$C_{22}$ fatty alcohol.

4. An aqueous conditioning shampoo composition according to claim 1, wherein the gel network comprises a quaternary ammonium compound having only one carbon chain of length $C_{12}$-$C_{30}$ and wherein the hydrophobic particulates have a melting point higher than said quaternary ammonium compound.

* * * * *